United States Patent
Beraud

(10) Patent No.: US 7,204,956 B1
(45) Date of Patent: Apr. 17, 2007

(54) METHOD FOR CONTROLLING THE OPERATION OF A HEAT-DISINFECTING DEVICE FOR WASTE, VIZ. BIOLOGICALLY HAZARDOUS WASTE

(75) Inventor: Christophe Beraud, Orange (FR)

(73) Assignee: Prontex Investments LLP, Societe de Droit Anglais, London (GB)

( * ) Notice: Subject to any disclaimer, the term of this patent is extended or adjusted under 35 U.S.C. 154(b) by 496 days.

(21) Appl. No.: 10/384,789

(22) Filed: Mar. 11, 2003

(51) Int. Cl.
*A61L 9/00* (2006.01)

(52) U.S. Cl. .............................. 422/3; 422/25; 422/38

(58) Field of Classification Search ................... 422/3, 422/25, 38, 107, 30, 114; 100/177
See application file for complete search history.

(56) References Cited

U.S. PATENT DOCUMENTS

| | | | | |
|---|---|---|---|---|
| 3,204,766 A | * | 9/1965 | Schmidt, Jr. ................. | 210/86 |
| 3,613,558 A | * | 10/1971 | Math ............................ | 100/35 |
| 4,860,958 A | * | 8/1989 | Yerman ....................... | 241/23 |
| 5,145,641 A | * | 9/1992 | Shelley ......................... | 422/26 |
| 5,207,994 A | * | 5/1993 | Suzuki et al. ................ | 422/307 |
| 5,348,704 A | * | 9/1994 | Tanaka ......................... | 422/22 |
| 5,507,177 A | * | 4/1996 | Focke .......................... | 73/49.3 |
| 2002/0108507 A1 | * | 8/2002 | May et al. .................... | 100/45 |

FOREIGN PATENT DOCUMENTS

WO   WO 9606728 A1  *  3/1996
WO   WO 9911299 A1  *  3/1999

* cited by examiner

*Primary Examiner*—Krisanne Jastrzab
(74) *Attorney, Agent, or Firm*—Egbert Law Offices

(57) ABSTRACT

The invention relates to a method for controlling the operation of such a heat-disinfecting device for waste, viz. biologically hazardous waste, on the one hand, including a mold inside which is placed waste and, on the other hand, being designed capable of ensuring compacting, heating and cooling this waste in this mold. This control method is characterized in that during compacting and before applying heating the presence of a non-compactable object in the mold is checked, in order to either complete compacting if no such non-compactable object is detected or to interrupt the process in the event such a non-compactable object is detected.

2 Claims, 1 Drawing Sheet

METHOD FOR CONTROLLING THE OPERATION OF A HEAT-DISINFECTING DEVICE FOR WASTE, VIZ. BIOLOGICALLY HAZARDOUS WASTE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

This invention relates to a method for controlling the operation of a heat-disinfecting device for waste, viz. biologically hazardous waste.

This invention applies to the field of waste treatment, in particular waste that can be biologically hazardous, viz. waste proceeding from the medical field.

BACKGROUND OF THE INVENTION

There are already known processes for treating such waste, which consist first of all in collecting this waste to convey it to a special processing unit, such as an incinerator or a heat-processing plant. In this respect, one should note that prior to such a treatment this waste undergoes a number of handling operations (crushing, classification, transporting . . . ) as well as very often an intermediate storage, which increases the risks, on the one hand, of a proliferation of pathogenic germs and, on the other hand, of contamination all along the processing line.

Another solution consists in treating the waste on the very site of its production. For this purpose there are known machines operating with an ozone thrust or using disinfecting solutions, such machines do however not allow disinfecting closed objects such as sampling needles into which disinfecting agents cannot penetrate. To cope with this drawback, there are known thermal machines, which have the drawback of either having to proceed to a previous crushing of the waste before heating it, with a view to a better heat transfer, or of having to heat it using overheated steam, or of using a radio-frequency source. In addition, such thermal machines are usually aimed at treating large quantities of waste (20 to 250 kg/h) and represent a heavy capital investment and require a large space, so that they are generally installed at a good distance from the site of generation of the waste, which once again gives rise to the problem of proliferation of germs resulting from transportation and an intermediate storage.

These machines are therefore in no way suited for being used by a practitioner, by a small sampling or analysis laboratory, which generate only a small quantity of waste daily. In such a case, such waste has to be transported, with the necessary precautions, to a disinfection plant, in order to ensure its treatment. This involves a particular high cost and is, moreover, not always possible for reasons of accessibility and distance of such a plant, e.g. for waste generated at an isolated place as on a ship or the like.

To cope with these drawbacks, there has been devised a heat-disinfecting device for waste, which is the object of FR-2,767,700, in this document being also disclosed a disinfecting method likely to be implemented by this device.

In this respect, it should be noted that said method includes a heat-disinfection step during which this waste (viz. placed in a polymeric bag) is placed into a mold forming a compacting area, then subjected to pressure, the gases released by compacting this waste being filtered before being discharged. The mold is then sealed and heating is applied, while simultaneously controlling the pressure and the temperature inside this mold. This heat-disinfection step also consists in that all the parts that have entered into contact with the waste are also disinfected and it is followed by a step of removal from the mold including cooling, return to the atmospheric pressure and evacuation of the compacted waste.

As regards said disinfecting device, it includes a compacting area into which a bag with waste is inserted, means for sealing the device, a heat insulation and viz. a heat-proof material, said compacting area including a piston provided with a hydraulic or mechanical jack actuated by a pump or an electric engine, a mold, a lid, means for filtering the gases released during compacting, heating means such as viz. electric resistors and/or varistors.

BRIEF SUMMARY OF THE INVENTION

The present invention regards, in fact, a number of improvements made to the above-mentioned device and method and relates, in particular, to a method for controlling the operation of such a heat-disinfecting device for waste, viz. biologically hazardous waste, on the one hand, comprised of a mold inside which is placed said waste and, on the other hand, designed capable of ensuring compacting, heating and cooling this waste in this mold. This control method is characterized in that during compacting and before applying heating the presence of a non-compactable object in the mold is checked, in order to either complete compacting if no such non-compactable object is detected or to interrupt the process in the event such a non-compactable object is detected.

According to another feature, the method also consists in that during the compacting the waste and before heating it the presence of liquid is checked, in order to either proceed with the compacting until it is interrupted, viz. when it is completed if the presence of no liquid is detected, or, in the event any liquid is detected, to proceed to checking the tightness of a bag inside which the waste has been placed, in order to interrupt the process in the event this bag is tight.

An additional feature consists in that in the absence of detecting a non-compactable object and/or in the absence of detecting liquid, the pressure inside the mold is determined during compacting in order to stop compacting when this pressure reaches a predetermined compacting-pressure value between 140 and 180 bars, preferable of about 160 bars.

According to another feature, after waste compacting has been interrupted and before its heating is ensured, assessing the thickness of a cake formed by this waste is proceeded to, in order to either continue processing by heating in the event the thickness of the cake is smaller than a predetermined thickness, or to interrupt the process in the event the thickness of the cake is larger than a predetermined thickness.

The advantages of the present invention reside in that the operation of the disinfecting device and/or the evolution of the disinfecting process are controlled by a method designed capable of controlling this device/process in a fully automatic way. Another advantage resides in that this method has been studied so as to allow taking into consideration various situations (presence of a non-compactable object, presence of alcohol . . . ) that could make the disinfecting process of the state of technique inoperative or unsatisfactory. Through this taking into consideration either a proper disinfection of this waste (if such is possible) or an interruption of the process by showing such an interruption (blocking of the device, activation of visual and/or sound-emitting means) is automatically proceeded to.

Further aims and advantages of this invention will become clear during the following description that relates to embodiments that are given only by way of examples and are not restrictive.

BRIEF DESCRIPTION OF THE SEVERAL VIEWS OF THE DRAWINGS

The understanding of this invention will be made easier when referring to the attached drawing.

DETAILED DESCRIPTION OF THE INVENTION

Figure 1:
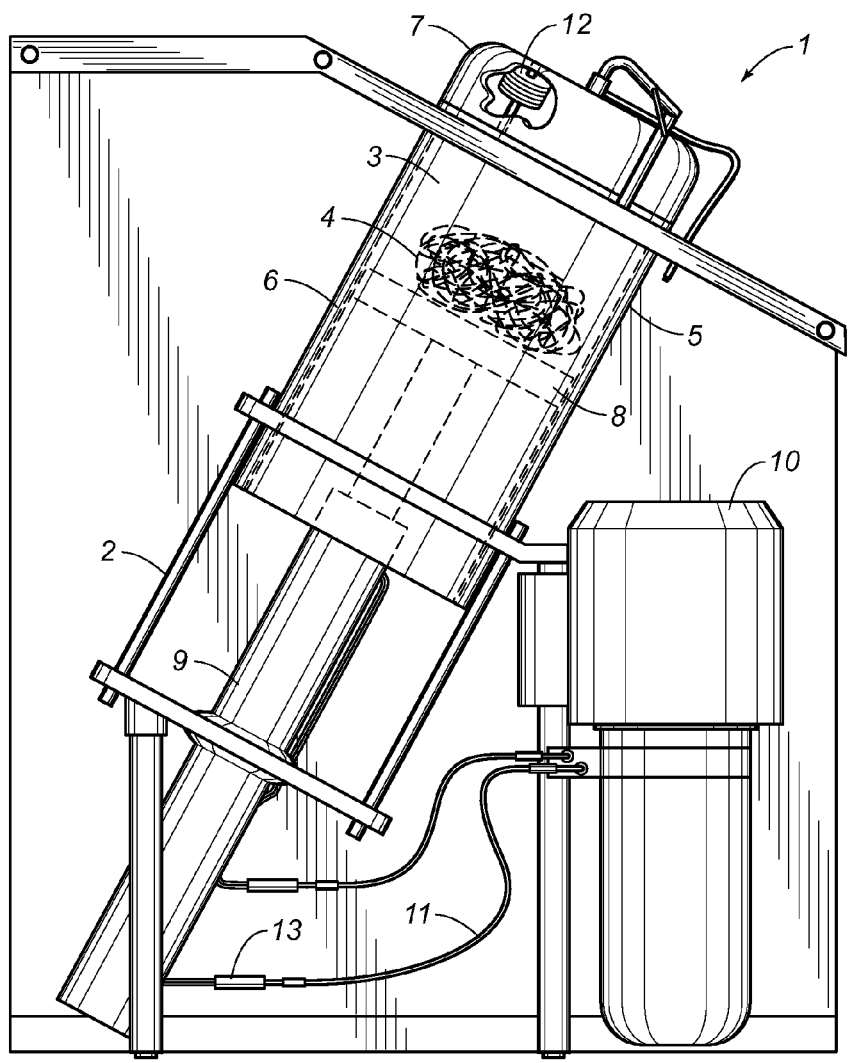
FIG. 1 is a schematic view of the disinfecting device capable of being controlled by the method according to the invention.

As can be seen in this figure, the disinfecting device 1 is in the form of a frame 2 receiving a compacting area 3 in which the waste 4 to be treated is placed.

Such a compacting area 3 is defined by a mold 5 defined by a side wall 6 topped by a lid 7 designed capable of ensuring the closing and opening of this mold 5 and, preferably, hingingly mounted with respect to the frame 2. Said lid 7 can also be completed with a device allowing ensuring its locking as well as with a device designed capable of allowing detecting a proper closing (or not) of this lid 7 (easily associated with e.g. a Hall-effect sensor).

This mold 5 also includes a piston 8 movably mounted (in particular in a tight way) with respect to said side wall 6 of this mold 5 and inside the latter 5.

In this respect, one should note that said piston 8 is located under or behind the waste to be treated and that, during compacting in the compacting area 3, said piston 8 ascends towards said lid 7, in order to compact the waste 4 against the latter 7. Also, when the treated waste 4 has to be discharged, said piston 8 ascends, so as to be capable of ejecting this waste 4 out of the compacting area 3, the lid 7 being open.

Said disinfecting device 1 also includes a jack 9 designed capable of operating said piston 8 and viz. mounted on said frame 2. This jack 9 can be of an electric type, but is preferably of a pneumatic or hydraulic type and is then connected to a (pneumatic or hydraulic) pump 10, this through an adequate (pneumatic or hydraulic) circuit 11.

An additional feature consists in that said piston 8 is completed with a skirt located under said piston 8 and designed capable of allowing detecting, as the case may be, the positioning of this piston 8 (in particular when the latter 8 is in lower position) or of a cake formed by compacted waste 4. Such a skirt is also designed capable of allowing disinfecting the equipment. One should note that this skirt as well as said piston 8 are preferably covered (during the compacting phase) with a jacket that is in turn covered with a teflon jacket insulator.

As regards said piston 8, it is also provided, in its lower portion, with a scraper segment made of stainless metal and having a diameter slightly larger than that of this piston 8. Such a scraper segment is designed capable of impeding the extrusion of waste 4 out of the compacting area 3, this at the level of said piston 8.

Another feature consists in that said mold 4, said piston 8 and said lid 7 (at least the portion of the latter in contact with the waste 4) are fully or at least partially made of or completely covered with metal having high thermal conductivity, e.g. aluminum.

An additional feature consists in that said mold 4, said piston 8 and said lid 7 (at least the portion of the latter in contact with the waste 4) are fully or at least partially made of or covered with a material that, on the one hand, has a sufficient hardness so as not to be damaged (scrapped or deteriorated) by sharp elements (in particular needles, scalpels or the like) and, on the other hand, is sufficiently resistant to corrosive agents (acids, bases, blood . . . ). Such a material is advantageously made of stainless metal, e.g. aluminum.

Another feature of this disinfecting device 1 consists in that it includes heating means defined at the level of said mold 5, in particular at the level of said piston 8, said lid 7 and/or said side wall 6.

Said heating means are formed by at least one electric resistor and/or at least one varistor and are eventually associated with temperature-adjusting means, viz. a thermostat. Such heating means can be designed capable of being controlled by the process according to the invention.

In this respect, one should note that said device 1 can, in addition, include a heat insulator that advantageously allows minimizing the heat losses and that is arranged at the level of said mold 5, in particular at the level of said piston 8 and/or around the side wall 6.

An additional feature consists in that said device 1 includes means designed capable of ensuring its tightness. Such means are defined by O-rings and/or expansible and/or inflatable seals and/or insulating valves. In this respect, one should note that a preferred embodiment consists in using expansible seals capable of ensuring, in an optimal way, the tightness thanks to their expansion under the action of heat.

Still another feature of the disinfecting device 1 consists in that it includes means 12 designed capable of ensuring a filtering of the gases released during compacting.

Such filter means 12 are formed of a very highly efficient filter formed e.g. and at least partially by a mineral membrane and/or by active carbon and/or by a teflon felt and/or by a steel-fiber felt.

A particular embodiment consists in that these filter means 12 include at least a first metallic cloth (viz. made of stainless steel, nominal mesh size between 70 and 110 microns, preferably 90 microns, wires with a diameter between 0.035 and 0.050 mm, preferably 0.043 mm), a dessicator (viz. in the form of granulates), a second metallic cloth (viz. made of stainless steel, nominal mesh size between 400 and 600 microns, preferably 500 microns, wires with a diameter between 0.280 and 0.340 mm, preferably 0.315 mm) and a filter. These filter means 12 can be completed with heating means (heating element or the like), so that the temperature of these means 12 is substantially equal to that of the treatment of the waste 4.

The filter means 12 are completed with at least one electrovalve allowing discharging the decontaminated gases and designed capable of being controlled by the process according to the invention.

In this respect, one should note that the filter means 12 (as well as the electrovalve or electrovalves and the eventual heating means that complete these means 12) are provided for at the level of said lid 7.

According to another feature of the invention, said disinfecting device 1 also includes means 13 capable of detecting the pressure. Such means 13 can be formed by at least one pressure gauge (viz. arrange on the hydraulic circuit 11) and/or by at least one stress gauge, viz. associated with said jack 9 (e.g. of an electric type).

Such pressure-detecting means 13 are designed capable of being controlled by the process according to the invention.

The device 1 includes, in addition, means designed capable of allowing assessing the thickness of the compacted waste 4 (viz. of a cake formed by such waste 4). Such assessing means include detecting means formed by an optoelectronic sensor (viz. a phototransistor) or the like, associated with said piston 8 and/or said skirt (in particular for detecting its position), and are designed capable of being controlled by the process according to the invention.

This device 1 includes, in addition, means capable of detecting the temperature prevailing at the level of the compacting area 3 (in particular inside the mold 5 and/or at the level of the side wall of the latter 5), these means being also designed capable of being controlled by the process according to the invention.

According to a preferred embodiment of the invention, the unit comprised of at least the piston 8, the mold 5 and the lid 7 is slanted according to an angle adapted so that the compacted waste 4 directly falls during the discharge, under the action of gravity, into a refuse bin placed at the proper location. The angle of inclination of the piston 8 is preferably at least 20° with respect to the vertical line. In addition to its function of facilitating the discharge of the compacted waste 4, this slanted arrangement allows saving space and facilitating inserting this waste 4.

In this respect, one should note that, according to a first embodiment of the invention, the waste 4 is covered with a preferably composite polymeric material after its insertion into the compacting area 3. However and according to a preferred embodiment, before it is inserted into the compacting area 4, this waste 4 is placed in a bag the composition of which is chosen according to the processing temperature of this waste 4. Such a bag is preferably made out of a preferably composite polymeric material, the outer surface of this bag being of polypropylene or polyamide, while its inner surface is of polyethylene.

Finally, the device 1 includes or is associated with data-processing means, viz. at least a microprocessor, capable of implementing a software designed capable of ensuring its control and/or its operation.

The disinfecting device 1 described above is designed capable of implementing a disinfecting process including a heat-disinfection step during which this waste 4 is placed in the mold 5 forming a compacting area 3, then subjected to pressure, the gases released during the compacting of this waste 4 being filtered before being discharged. The mold 5 is then sealed and heating (temperature between 100 and 200° C.) is applied while simultaneously monitoring the pressure and the temperature inside this mold 5. This heat-disinfection step also consists in that all the parts (5, 7, 8 . . . ) having been in contact with the waste 4 are also disinfected and it is followed by a step of removal from the mold including cooling down, return to the atmospheric pressure and discharge of the compacted waste 4.

It should be noted that the present invention regards in particular a method for controlling the operation of a heat-disinfecting device for waste, viz. biologically hazardous waste and/or of the above-mentioned type. Such a device is in particular comprised of a mold inside which said waste is placed and which is designed capable of ensuring compacting, heating and cooling down this waste in this mold.

In fact and as results from the following description, this process is in particular capable of ensuring the control of the operation of the disinfecting device 1 as described above, however without this invention being limited to it.

According to a feature of the invention, this method is characterized in that during compacting and before applying heating the presence of a non-compactable object in the mold 5 is checked.

Such checking allows, in the event such a non-compactable object is detected, interrupting the process of control, viz. waiting for a command to continue this process or a command to remove the waste from the mold 5. Therefore, in the event of such a detection, a visual or sound signal characteristic of the presence of a non-compactable object in the mold 5 can be emitted. In the event of such a detection, such a detection can also be stored into a memory device said control device 1 includes.

Such checking also allows, in the event no such non-compactable object is detected, to continue compacting the waste, viz. while waiting a command for heating this waste 4 or in order to directly and automatically proceed to such heating.

In this respect, it should be noted that the compacting of the waste 4 is finished when the pressure detected in the mold 5 reaches a predetermined compacting-pressure value, between 140 and 180 bars, preferably about 160 bars. Thus, when such a pressure value is detected in the mold 5, the operation of the compacting means (8, 9) is stopped, viz. waiting for a command to heat the waste 4 or in order to proceed to such a heating.

It should be noted that when the presence of a non-compactable object in the mold 5 is checked, an increase of the pressure inside this mold 5 is periodically determined (preferably every 0.05 second) during compacting, and this increase in pressure is compared with a predetermined set value (preferably 10 bars), in order to control, according to the result of this comparison, as the case may be, the continuation or the interruption of the compacting, even the interruption of the process of control of the device 1.

In fact, when the increase in pressure is lower than the set value, a command is given to continue compacting.

However, when this increase in pressure is higher than said set value, compacting is interrupted, even the control of the process is interrupted, viz. waiting for a command to proceed with the process or to withdraw the waste 4. In addition and when a non-compactable object is detected, a visual and/or sound signal can also be emitted.

According to another feature of the method, during the compacting of the waste 4 and before the heating of this waste 4 is ensured, the presence of liquid, viz. of water or water-based liquid, is checked.

Such checking allows, in the event no liquid is detected, continuing compacting until it is interrupted, viz. upon completion.

This checking also allows, in the event a liquid is detected, proceeding to checking the tightness of a bag inside which the waste has been placed, in order to interrupt the process of control of the device if this bag is tight, viz. waiting for a command to continue this process or a command to withdraw the waste 4 from the mold 5.

In fact, when the tightness of such a bag is checked, the drawing back of the piston 8 (viz. without connecting the device to the air) is ensured for some period of time (preferable of about 1.4 seconds). A comparison of this period of time with a set value is then ensured and when this period of time is larger than said set value, it is assumed the bag is tight.

It should be noted that checking the presence of a non-compactable object as well as checking the presence of liquid are ensured preferably during the full period of compacting of the waste 4, this punctually, periodically, even permanently.

Therefore and according to another feature of the invention, the process consists in that in the absence of detection of a non-compactable object and/or in the absence of detection of liquid, the pressure inside the mold 5 is determined during compacting of the waste so that compacting is ended when this pressure reaches a predetermined compacting-pressure value between 140 and 180 bars, preferably of about 160 bars.

In fact, the pressure inside the mold 5 is determined by proceeding to measuring the pressure at the level either of a sensor arranged on the hydraulic circuit of the jack 9 or of a stress gauge arranged on a mechanical jack.

Still another feature of the invention consists in that after interrupting the compacting of the waste 4 and before ensuring its heating, an assessment is made of the thickness of a cake formed by this waste, viz. placed in a bag.

In fact, this assessment viz. allows, in the event of a cake thickness lower than a predetermined thickness (viz. between 7 and 13 cm, preferably of about 10 cm), to continue the process of control of the device 1 by ensuring heating of the waste 4.

However, when the thickness of such a cake is larger than this predetermined thickness, the process is interrupted, viz. waiting for a command to continue this process or a command to remove the waste 4 from the mold 5.

In order to proceed to such an assessment, the mold 5 includes detecting means, preferably formed of an optoelectronic sensor (viz. a phototransistor).

Hence, upon interrupting the compacting, the position of the piston 8 (even the position of a skirt the piston 8 is provided with) with respect to this detecting means is detected.

Thus, when this piston 8 (or its skirt) is located in front of the detecting means, it is assumed that the thickness of the cake is larger than the predetermined thickness and the process is interrupted.

When the piston 8 (or its skirt) is located below (or, depending on the configuration of the device, above) the detecting means, it is assumed that the thickness of the cake is smaller than said predetermined thickness and either the waste 4 is heated, in the absence of detection of a non-compactable object during compacting, or, in the event a non-compactable object is detected during compacting, the process is interrupted, viz. waiting for a command to continue this process or a command to remove the waste 4 from the mold 5.

In fact and generally, it should be noted that when the process is interrupted, the device 1 is put in stand-by, waiting for either a command to open the mold 5 for removing the waste 4 or for a command to continue the process by heating this waste 4.

According to another feature of the invention, when heating of the waste 4 is ensured, first of all at least part of the device 1 is brought to a predetermined temperature, to apply, afterwards, a level of heating for a predetermined period of time.

In fact, one embodiment consists in heating this waste by ensuring heating of the piston 8 (eventually even of a lid 7 closing the device 1) and/or of the mold 5, this through electric resistors and/or varistors the mold 5 and/or this piston 8 (and/or the lid 7) include.

It should be noted that, according to a particular embodiment, before proceeding to applying a level of heating, it is ensured that the temperature of the mold 5 and/or of the piston 8 (and/or of the lid 7) is checked.

Such checking allows ensuring a control of this temperature, with a view to starting the level only when this temperature is comprised between 145° C. and 160° C., preferably comprised between 150° C. and 153° C.

Such checking also allows proceeding to interrupting the process when said temperature exceeds a determined so-called safety temperature (viz. of about 170° C.).

As regards said level of heating, it is established for a period of time comprised between 30 minutes and one hour, preferably of about 45 minutes.

According to another feature of the invention, the duration of the level of heating is checked, in order to interrupt the process in the event a predetermined period of time (e.g. two hours) is exceeded.

Still another feature consists in that the temperature is monitored during the level of heating, in order to proceed to interrupting the process when said temperature exceeds the above-mentioned safety temperature.

An additional feature relates to the fact that the pressure is checked during the heating of the waste 4 (viz. during the bringing up to the temperature of the level and/or during the level of heating).

Such a pressure checking allows, in the event a pressure higher than a predetermined pressure is detected, storing such a detection into a memory device the device 1 includes, even, eventually and according to a particular embodiment of the invention, proceeding to interrupting the process (predetermined pressure corresponding to a safety pressure, e.g. of about 130 bars).

In this respect, it should be noted that detecting a pressure higher than this predetermined pressure value (preferably of about 120 bars) allows e.g. showing the presence of alcohol in the waste 4.

According to another feature of the invention, the method consists in that after having ensured the heating of the waste 4 and before ensuring a cooling down, the pressure inside the mold 5 is checked.

Such checking allows interrupting the process of control of the device 1 when the pressure is lower than a determined pressure value (lower than 34 bars, preferably lower than 30 bars).

In addition, such monitoring allows proceeding to cooling down the waste 4 when the pressure is higher than this determined pressure value.

In this respect, it should be noted that a cooling down of this waste is proceeded to by ensuring the cooling down of the mold 5, either subjecting the latter 5 to a ventilation or by cooling the latter 5 by means of a heat-carrying liquid, this to a predetermined final cooling temperature (comprised between 40 and 80° C., preferably of about 60° C.).

Such a heat-carrying liquid is capable of flowing in a conduct associated with said mold 5 (viz. a coil, e.g. made of copper, surrounding the jacket of this mold 5) and connected to a cooling aggregate (even to a heat-carrying liquid tank) said device 1 includes.

According to another feature of the invention, during the cooling and when the temperature of the mold reaches a predetermined intermediate temperature (comprised between 90° C. to 110° C., preferably of about 100° C.), a re-compacting of the waste 4 can be proceeded to.

In this respect, it should be noted that such a re-compacting is ensured when no liquid has been detected during the compacting and/or when no alcohol has been detected during the heating of the waste 4.

In addition, such a re-compacting is preferably ensured when during the compacting preceding the heating of the waste 4 the compacting pressure has not reached the above-mentioned predetermined compacting-pressure value (comprised between 140 and 180 bars, preferably of about 160 bars).

In fact, this re-compacting is then carried out until such a predetermined compacting-pressure value is reached.

Such a re-compacting is ensured without connecting the mold 5 to the air, viz. while ensuring a detection of non-compactable objects and/or a detection of presence of liquid as above-mentioned.

The cooling of the waste 4 is continued after such a re-compacting.

It should be noted, in addition, that during cooling down of this waste 4, checking the time of this cooling down and/or of the temperature and/or of the pressure in the mold 5 is proceeded to, in order to interrupt the process of control of the device 1 in the event a determined cooling time (e.g. of about 3 hours) and/or a determined temperature (e.g. the above-mentioned safety temperature) and/or a determined pressure (e.g. the above-mentioned safety pressure) are exceeded.

According to another feature of the invention, the method consists in that upon cooling down of the mold 5 to the predetermined final cooling temperature a return to the atmospheric pressure of this mold 5 is ensured and an opening of the latter 5 is authorized, in order to remove the treated and decontaminated waste 4.

However, when at the end of the cooling down to the predetermined final cooling temperature the pressure detected inside the mold 5 is higher than a predetermined pressure value, the process is interrupted.

In addition, at the end of the cooling down to the predetermined final cooling temperature the process is interrupted if a presence of alcohol inside this mold 5 has been detected during the beating of the waste.

According to another feature of the invention, when an interruption of the process of control is ensured during the compacting or heating of the waste 4, during its cooling down or at the end of this cooling down, this interruption can be enhanced by ensuring the blocking of the heat-disinfecting device while waiting for an operator from the customer service to intervene.

Still another feature consists in that said device 1 can be provided with visual (e.g. a LED or similar) and/or sound signaling means designed capable of being activated in the event the process of control is interrupted. The activation of such signaling means indicates that the waste 4 contained in the mold 5 is not treated.

An additional feature consists in that the process can provide for a protocol for authorizing, as the case may be, a start of the disinfecting device 1 and/or the opening of the lid 7 of the latter 1, viz. upon an interruption of the disinfecting process, e.g. when the latter has been completed or, on the other hand, when the latter has been interrupted for any of the above-mentioned reasons.

In this respect, such a protocol can consist in inserting a code, viz. through entering such a code or through an authentication by means of a card, badge or the like.

The method according to the invention can then foresee that in the absence of an authorization said device 1 is made inoperative and requires the intervention of an operator from the customer service.

Finally, it should be noted that this process is designed capable of being managed or controlled through a software implemented by data-processing means, viz. at least one microprocessor associated to the heat-disinfecting device 1 or which the latter 1 includes.

The present invention thus also relates to a computer program including means for performing the above process steps, this when said program is implemented by data-processing means.

I claim:

1. A method of controlling a heat-disinfecting device for waste comprising:
   placing the waste into a bag within a mold;
   compacting the waste in said mold;
   checking for a presence of a non-compactable object in the waste by periodically sensing an increase in pressure in said mold during said compacting;
   detecting a presence of a liquid in said mold;
   checking a compression of said bag against said mold;
   comparing the increase in pressure to a predetermined pressure value; and
   interrupting the compacting of the waste and an application of heat if either the increase in pressure is greater than the predetermined pressure value or if the compression of the bag against the mold exceeds a predetermined compression value, said predetermined pressure value being between 140 and 180 bars.

2. A method of controlling a heat-disinfecting device for waste comprising:
   placing the waste in a mold;
   compacting the waste in said mold;
   checking for a presence of a non-compactable object in the waste by periodically sensing an increase in pressure in said mold during said compacting;
   sensing a thickness of a cake formed by the compacted waste;
   comparing the increase in pressure to a predetermined pressure value;
   interrupting the compacting of the waste and an application of heat if either the increase in pressure is greater than said predetermined pressure value of if the thickness of said cake exceed a predetermined thickness value, said step of interrupting comprising:
      placing the stop of compacting in a stand-by mode; and
      heating the waste subsequent to said step of compacting, said step of heating the waste comprising:
         sensing a pressure within said mold during the step of heating;
         comparing the sensed pressure with a predetermined value; and
         cooling the heated waste in the mold if the sensed pressure is higher than said predetermined value, said step of cooling comprising:
            ventilating said mold so as to cool the waste in said mold to a predetermined final cooling temperature;
   recompacting the waste in said mold when a temperature of said mold reaches a predetermined intermediate temperature, said recompacting occurring without exposing an interior of said mold to air;
   returning said mold to atmospheric pressure;
   opening said mold; and
   removing the recompacted waste from the opened mold.

* * * * *